United States Patent
Rigas (10) Patent No.: US 12,295,963 B2
(45) Date of Patent: *May 13, 2025

(54) TREATING PAIN ASSOCIATED WITH DIABETIC PERIPHERAL NEUROPATHY

(71) Applicant: MEDICON PHARMACEUTICALS, INC., Setauket, NY (US)

(72) Inventor: Basil Rigas, Setauket, NY (US)

(73) Assignee: MEDICON PHARMACEUTICALS, INC., Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/515,743

(22) Filed: Nov. 21, 2023

(65) Prior Publication Data

US 2024/0100073 A1    Mar. 28, 2024

Related U.S. Application Data

(63) Continuation of application No. PCT/US2022/072497, filed on May 23, 2022.

(60) Provisional application No. 63/192,248, filed on May 24, 2021.

(51) Int. Cl.
*A61K 31/661* (2006.01)
*A61P 25/02* (2006.01)
*A61P 25/04* (2006.01)

(52) U.S. Cl.
CPC ............ *A61K 31/661* (2013.01); *A61P 25/02* (2018.01); *A61P 25/04* (2018.01)

(58) Field of Classification Search
CPC .............................. A61K 31/661; A61P 25/02
USPC .................................................. 514/143, 141
See application file for complete search history.

(56) References Cited

U.S. PATENT DOCUMENTS

| 8,236,820 B2 | 8/2012 | Rigas |
| 2006/0241074 A1 | 10/2006 | Woolf |
| 2013/0225529 A1 | 8/2013 | Rigas |
| 2024/0180936 A1 | 6/2024 | Rigas |

FOREIGN PATENT DOCUMENTS

| CN | 101820755 | 9/2010 | |
| CN | 105658651 | 6/2016 | |
| WO | 2013067591 | 5/2013 | |
| WO | WO 2014/047592 A2 * | 3/2014 | ........... A61K 31/661 |
| WO | 2017106714 | 6/2017 | |
| WO | 2018064354 | 4/2018 | |
| WO | 2019067919 | 4/2019 | |
| WO | 2020101790 | 5/2020 | |
| WO | 2022251805 | 12/2022 | |
| WO | 2022251806 | 12/2022 | |

OTHER PUBLICATIONS

Bonin, R. et al., "A simplified up-down method (SUDO) for measuring mechanical nociception in rodents using von Frey filaments", Mol Pain, 10:26, (2014).
Dobretsov, M. et al., "Animal Models of Diabetic Neuropathic Pain", Curr Protoc Neurosci., 29(1):147-69, (2011).
International Application No. PCT/US2022/072497; International Preliminary Report on Patentability, date of issuance Dec. 7, 2023, 7 pages.
International Application No. PCT/US2022/072497; International Search Report and Written Opinion of the International Searching Authority, date of mailing Sep. 2, 2022; 10 pages.
Mackenzie, G. et al., "Phospho-sulindac (OXT-328), a novel sulindac derivative, is safe and effective in colon cancer prevention in mice", 139(4):1320-32, (2010).
Matteolabakis, G. et al., "Topically applied phospho-sulindac hydrogel is efficacious and safe in the treatment of experimental arthritis in rats", Pharm Res., 30(6):1471-82, (2013).
Moore, R. et al., "Single dose oral analgesics for acute postoperative pain in adults—an overview of Cochrane reviews (Review)", Cochrane Database Syst Rev., 2015(9):CD008659, pp. 1-36, (2015).
Morrow, T. et al., "Animal Models of Painful Diabetic Neuropathy: The STZ Rat Model", Curr Prot Neurosci., 9(18):1-11, (2004).
Wen, Z. et al., "The ocular pharmacokinetics and biodistribution of phospho-sulindac (OXT-328) formulated in nanoparticles: Enhanced and targeted tissue drug delivery", Int J Pharm., 557:273-9, (2019).
Xie, G. et al., "The metabolism and pharmacokinetics of phospho-sulindac (OXT-328) and the effect of difluoromethylornithine", Br J Pharmacol., 165(7):2152-66, (2012).
Zochodne, D. et al., "The Influence of Sulindac on Experimental Streptozotocin-Induced Diabetic Neuropathy", Can J Neur Sci., 21(3):194-202, (1994).
Argyriou, A. et al., "Bortezomib-induced peripheral neuropathy in multiple myeloma: a comprehensive review of the literature", Blood, Am Soc Hematol., 112(5):1593-9, (2008).
Bagdas, D. et al., "The role of alpha5 nicotinic acetylcholine receptors in mouse models of chronic inflammatory and neuropathic pain", Biochem Pharmacol., 97(4):590-600, (2015).
Carozzi, V. et al., "Neurophysiological and neuropathological characterization of new murine models of chemotherapy-induced chronic peripheral neuropathies", Exp Neurol., 226(2):301-9, (2010).
Chaplan, S. et al., "Quantitative assessment of tactile allodynia in the rat paw", J Neurosci Methods, 53(1):55-63, (1994).
Colvin, L., "Chemotherapy-induced peripheral neuropathy: where are we now?", Pain, 160 Suppl 1(Suppl 1):S1-S10, (2019).
Currie, G. et al., "Animal models of chemotherapy-induced peripheral neuropathy: A machine-assisted systematic review and meta-analysis", PLOS Biol., 17(5):e3000243, (2019).
Eldridge, S. et al., "A Comparative Review of Chemotherapy-Induced Peripheral Neuropathy in In Vivo and In Vitro Models", Toxicol Pathol., 48(1):190-201, (2020).

(Continued)

*Primary Examiner* — Charanjit Aulakh
(74) *Attorney, Agent, or Firm* — Weaver Austin Villeneuve & Sampson LLP (57) ABSTRACT

The invention features methods of preventing and/or treating neuropathic pain associated with diabetic peripheral neuropathy (DPN).

29 Claims, 6 Drawing Sheets

(56) References Cited

OTHER PUBLICATIONS

Hidaka, T. et al., "Herbal medicine Shakuyaku-kanzo-to reduces paclitaxel-induced painful peripheral neuropathy in mice", Eur J Pain, 13(1):22-7, (2009).
International Application No. PCT/US2022/072496; International Preliminary Report on Patentability, date of issuance Dec. 7, 2023, 7 pages.
International Application No. PCT/US2022/072496; International Search Report and Written Opinion of the International Searching Authority, date of mailing Sep. 2, 2022; 10 pages.
Kaley, T. et al., "Therapy of chemotherapy-induced peripheral neuropathy", Br J Haematol., 145(1):3-14, (2009).
Toma, W. et al., "Effects of paclitaxel on the development of neuropathy and affective behaviors in the mouse", Neuropharmacology, 117:305-15, (2017).
U.S. Appl. No. 18/515,734; Non-Final Office Action, dated Jul. 3, 2024; 17 pages.
U.S. Appl. No. 18/515,734; Notice of Allowance, dated Oct. 17, 2024; 18 pages.

* cited by examiner

FIG. 1
DPN Treatment

DPN Prevention

TREATING PAIN ASSOCIATED WITH DIABETIC PERIPHERAL NEUROPATHY

This application is a bypass continuation of International Application No. PCT/US2022/072497, filed May 23, 2022, which claims the benefit of U.S. provisional application 63/192,248, filed May 24, 2021, the complete contents of which are incorporated herein by reference for all purposes.

FIELD OF THE INVENTION

The invention relates to compounds and their use in the treatment of neuropathic pain associated with diabetic peripheral neuropathy (DPN).

BACKGROUND OF THE INVENTION

Neuropathies are diseases or abnormalities of the nervous system, which afflict more than 20 million Americans. Indeed, according to recent studies, it is observed that neuropathic pain affects about 1 in every 10 adults and the economic burden for treating this pain is increasing.

Neuropathies are associated with the development of neuropathic pain. Neuropathic pain can occur as a result of damage to the peripheral or central nervous system. Peripheral neuropathic pain is caused by damage to nerve structures such as peripheral nerve endings or nociceptors which become extremely sensitive to stimulation and which can generate pulses in the absence of stimulation. The damage can occur for many reasons, such as diseases such as diabetes (i.e., DPN), chemotherapy treatments, as well as advanced-stage cancers, viruses (e.g., herpes zoster or HIV), and physical injury (e.g., an accident or surgery).

The lesion of the peripheral nerve can result in pathological states characterized by the presence of continuous spontaneous pain often associated with hyperalgesia (increased response to harmful stimuli) and allodynia (pain induced by a non-painful stimulus). Hyperalgesia and allodynia have been linked to central sensitisation, in which CNS nociceptive neurons display increased excitability due to a reduced stimulation threshold, triggered by persistent input or peripheral injury. Central sensitisation is implicated in the generation and maintenance of neuropathic pain associated with peripheral neuropathies.

From a symptomatic perspective, peripheral neuropathies may cause sharp pains, dull aches, a sensation of painful burning or cold, paraesthesia, a loss of proprioception, numbness, or even a loss of the sensation of pain.

There is currently a worldwide need for additional pain therapy, and neuropathic pain has developed into a major health problem in broad areas of the population.

Treatment of neuropathic pain is often attempted using so-called unconventional analgesics such as antidepressants like duloxetine and amitriptyline, or anti-epileptics like gabapentin or pregabalin. Additionally, topical anaesthetics, including lidocaine, have been used for the treatment and management of neuropathic pain. Despite evidence to the contrary, nonsteroidal anti-inflammatory drugs (NSAIDs) are widely used in the management of neuropathic pain. Upon a review of recent clinical trials, however, there was no indication of any significant pain reduction with NSAIDs in neuropathic pain patients (Moore et al. Cochrane Database of Systematic Reviews (2015); 10: 1-25), with no clinical outcome showing a statistically significant difference between NSAIDs and placebo. The Cochrane Library concluded that NSAIDs should not be recommended for the treatment of neuropathic pain.

DPN is the peripheral nerve damage caused by diabetes, and represents one of the most serious complications of the disease. About half of all people with diabetes have some form of nerve damage, with hyperglycaemia being a main cause of peripheral neuropathy in DPN. DPN can affect both small nerves and large nerves, which protect the human body by sending signals about pain and temperature changes to brain, and which detect touch, pressure, and help to keep balance. Clinical guidelines recommend pain relief in painful diabetic neuropathy through the use of antidepressants (e.g., duloxetine) and/or antiepileptics (e.g., gabapentin and pregabalin), as well as opioids and topical agents such as capsaicin. The current treatments for the pain associated with DPN have limited efficacy and may cause significant side effects.

Therefore, there is a strong need for compounds that treat and/or prevent pain associated with peripheral neuropathies, in particular DPN.

SUMMARY OF THE INVENTION

The inventor has surprisingly found that phosphosulindac (PS) is effective in the treatment and prevention of pain associated with DPN.

PS is a non-steroidal compound with anti-inflammatory activity. However, unlike its parent compound, the NSAID sulindac, PS does not inhibit COX-1 and COX-2 expression and so is not a typical NSAID. PS has previously been shown to have anti-cancer and anti-inflammatory properties via its inhibition of activation of NF-κB and changes in MAPK signalling branches, as well as an activity in treating rheumatoid arthritis in inflammatory mouse models via suppression of key pro-inflammatory signalling pathways (Mackenzie et al. (2010) *Gastroenterology* 139(4): 1320-32 and Mattheolabakis et al. (2013) *Pharm Res* 30(6): 1471-82). WO 2019/067919 suggests an anti-inflammatory activity of PS in an acute model of dry eye disease (DED). Furthermore, in this model, PS is seen to restore suppressed ocular sensitivity in DED, suggesting a role of PS in increasing rather than reducing nociception. Although PS is not a typical NSAID as noted above, it demonstrated similar activity to NSAIDs when administered to normal eyes in the DED model. However, these observations fail to suggest a role for PS in the treatment of neuropathic pain associated with DPN. Furthermore, clinical guidance in the field recommends avoiding the use of NSAIDs for the treatment of all types of neuropathic pain, and so anti-inflammatory activity alone is considered not sufficient therapeutically.

Nevertheless, the present inventor considered the activity of PS in a specific animal model of neuropathic pain and demonstrated a surprising therapeutic efficacy, equivalent to direct acting nerve blocking anaesthetics, e.g., lidocaine and pregabalin. Specific animal models are important during the development of therapies for treating neuropathic pain. Indeed, given the pathogenesis of pain associated with peripheral neuropathy, observations of efficacy of a particular compound in an alternative pain model cannot indicate the utility of that compound in treating neuropathic pain. In line with this, it is not possible to extrapolate the use of effective drugs from other forms of neuropathic pain to the neuropathic pain of particular interest, even if the clinical syndrome is similar. For example, gabapentin shows different efficacy in the treatment of different forms of neuropathic pain. Accordingly, the animal model used in early testing before further clinical development is crucial. Based on the specific animal model of DPN neuropathic pain, the observations herein demonstrate an unprecedented efficacy of PS in the treatment and/or prevention of neuropathic pain associated with DPN.

Therefore, in a first aspect, the invention provides a method of treating and/or preventing neuropathic pain associated with DPN comprising administering a therapeutically effective amount of PS to a subject in need thereof such that neuropathic pain associated with DPN is treated and/or prevented.

In some embodiments, the PS is the sulfoxide form of PS. Therefore, the PS may have the formula I (PS-I):

(I)

In other embodiments, the PS is the sulfide form of PS. Therefore, the PS may have the formula II (PS-II):

(II)

Herein, references to 'phosphosulindac' or to 'PS' encompass both PS-I and PS-II. The sulfide form of the compound is preferred. The compounds of formulae I and II are described in U.S. Pat. No. 8,236,820, which is hereby incorporated by reference in its entirety.

As noted above, nerve damage associated with DPN may result in over-activation of pain signalling pathways resulting in sensitisation of peripheral and/or central neurons, which display reduced stimulation thresholds. Accordingly, subjects having DPN may experience pain as a consequence of this sensitisation, for example, experiencing pain induced by a non-painful stimulus (allodynia) or experiencing heightened pain in response to a harmful stimulus (hyperalgesia). On the basis of the observations herein, PS may have a direct analgesic effect, for example by reducing the neuronal signalling involved in the sensation of pain. Furthermore, PS may reduce pain generated via peripheral sensitisation or via central sensitisation. Accordingly, PS may reduce or prevent pain signalling occurring centrally. The PS may reduce or prevent pain signalling occurring in the sciatic nerve. The PS may reduce or prevent pain signalling occurring in the dorsal root ganglion. Given that PS is shown to ascend peripheral neurons towards the spinal cord, PS may reduce or prevent pain signalling occurring in the spinal cord. In some embodiments, the neuropathic pain is allodynia. The allodynia may be in response to mechanical and/or thermal stimuli. In addition, in some embodiments, the neuropathic pain is hyperalgesia.

PS may be formulated into a pharmaceutical composition for use in the invention. In some embodiments, the pharmaceutical composition comprises PS and one or more pharmaceutically acceptable excipients. PS may be formulated for topical administration, in particular for topical administration to a subject's upper and lower limbs (i.e., to cover the stocking and glove distribution).

DETAILED DESCRIPTION OF THE INVENTION

Definitions

The following definitions of types of pain are according to the International Association for the Study of Pain (IASP). "Pain" is an unpleasant sensory and emotional experience associated with, or resembling that associated with, actual or potential tissue damage. "Neuropathic pain" is caused by a lesion or disease of the somatosensory nervous system. Neuropathic pain is a clinical description (and not a diagnosis) which requires a demonstrable lesion or a disease that satisfies established neurological diagnostic criteria. Patients with neuropathic pain may experience one or more sensations described as heat, burning, throbbing, shooting, stabbing, sharpness, cramping, aching, tingling, numbness, or pins and needles. The term "lesion of the somatosensory nervous system" is commonly used when diagnostic investigations (e.g., imaging, neurophysiology, biopsies, lab tests) reveal an abnormality or when there was obvious trauma. The term "disease of the somatosensory nervous system" is commonly used when the underlying cause of the lesion is known (e.g., stroke, vasculitis, diabetes mellitus, genetic abnormality). "Peripheral neuropathic pain" is pain caused by a lesion or disease of the peripheral somatosensory nervous system. "Central neuropathic pain" is pain caused by a lesion or disease of the central somatosensory nervous system. "Central sensitisation" refers to increased responsiveness of nociceptive neurons in the central nervous system to their normal or subthreshold afferent input. "Peripheral sensitisation" refers to increased responsiveness and reduced threshold of nociceptive neurons in the periphery to the stimulation of their receptive fields. "Allodynia" is pain due to a stimulus that does not normally provoke pain. "Hyperalgesia" is increased pain from a stimulus that normally provokes pain.

In general, the term "disease" refers to a state of being or health status of a patient or subject capable of being treated using the methods provided herein.

The term "therapeutically effective amount" refers to that amount of a compound or combination of compounds as described herein that is sufficient to effect the intended application including, but not limited to, treating and/or preventing the disease.

"Pharmaceutically acceptable excipient" is intended to include any and all solvents, dispersion media, coatings, antibacterial and antifungal agents, isotonic and absorption delaying agents, and inert ingredients included in pharmaceutical compositions. The use of such pharmaceutically acceptable excipients for formulating active pharmaceutical ingredients is well known in the art. Except insofar as any conventional pharmaceutically acceptable excipient is incompatible with PS, its use in the therapeutic compositions of the invention is contemplated.

Use of the term "about" when referring to a number is optional, and means that the number referred to is an approximation within typical experimental variability (or within statistical experimental error), and thus the number may vary accordingly.

The term "comprising" encompasses "including" as well as "consisting", e.g., a composition "comprising" X may consist exclusively of X or may include something additional (e.g., X+Y).

Pain Associated with Diabetic Peripheral Neuropathy

The pathology occurring in diabetic patients, in particular hyperglycaemia, can cause damage to neurons resulting in peripheral neuropathy and associated neuropathic pain. The neuropathic pain in these patients develops over time and is often worse in patients with long-standing disease, and may include stabbing pain, burning pain, and/or drilling pain. In some embodiments, the invention provides a method of preventing neuropathic pain associated with DPN, comprising administering a therapeutically effective amount of PS to a subject in need thereof such that neuropathic pain associated with DPN is prevented. In other embodiments, the invention provides a method of treating neuropathic pain associated with DPN, comprising administering a therapeutically effective amount of PS to a subject in need thereof such that neuropathic pain associated with DPN is treated. As DPN develops in diabetes patients over time, a subject may experience worsening neuropathic pain over time and so the subject would benefit from an analgesic which can both treat the ongoing neuropathic pain and prevent generation of further neuropathic pain. Therefore, in some embodiments, PS can be used in the treatment and prevention of neuropathic pain associated with DPN. In line with the above, the invention provides PS for use in the treatment and/or prevention of neuropathic pain associated with DPN. Furthermore, the invention provides the use of PS for the manufacture of a medicament for the treatment and/or prevention of neuropathic pain associated with DPN.

On the basis of the observations herein, PS has a direct analgesic effect on neuropathic pain associated with DPN. The neuropathic pain associated with DPN may be a stabbing pain, burning pain, and/or drilling pain. A subject with DPN may experience neuropathic pain constantly present and symmetric in the lower and upper limbs. In treating neuropathic pain associated with DPN, PS may reduce or eliminate the neuropathic pain. In treating the neuropathic pain associated with DPN, PS may also reduce or eliminate one or more of the sensory symptoms associated with DPN. In preventing neuropathic pain associated with DPN, PS may decrease the incidence of the neuropathic pain. In preventing neuropathic pain associated with DPN, PS may also decrease the incidence of one or more of the sensory symptoms associated with DPN.

The sensory symptoms of DPN include paraesthesia (e.g., numbness, tingling, pricking, or formication), burning sensations, or shooting (i.e., electric shock-like) sensations. DPN usually affects extremities like feet, hands, legs, and arms, where nerve fibres are the longest and most numerous, and patients often have a 'stocking and glove' distribution. Even if the sensory symptoms experienced by a subject with DPN are not considered painful (or do not reach a threshold necessary to be considered pain per se), PS can be used to reduce, eliminate, or decrease the incidence of any one or more of the sensory symptoms experienced by a subject with DPN, including those listed above. PS can be used to reduce, eliminate, or decrease the incidence of the stocking and glove distribution in a subject with DPN.

As noted above, the neuropathic pain associated with DPN may be a consequence of central sensitisation, resulting in allodynia and/or hyperalgesia. PS may reduce, eliminate, or decrease the incidence of the neuronal signalling involved in the sensation of pain in a subject with DPN. The PS may reduce, eliminate, or decrease the incidence of pain generated via peripheral sensitisation or via central sensitisation. Accordingly, the PS may reduce, eliminate, or decrease the incidence of pain signalling occurring centrally. The PS may reduce, eliminate, or decrease the incidence of pain signalling occurring in the sciatic nerve. The PS may reduce, eliminate, or decrease the incidence of pain signalling occurring in the dorsal root ganglion. Given that PS is shown to ascend peripheral neurons towards the spinal cord, PS may reduce, eliminate, or decrease the incidence of pain signalling occurring in the spinal cord. The neuropathic pain in a subject with DPN may be allodynia (e.g., mechanical or thermal allodynia). Additionally or alternatively, the neuropathic pain in a subject with DPN may be hyperalgesia.

Neuropathic pain in a patient with DPN can be measured on a visual analogue pain scale or using any other appropriate method in the art.

Pharmaceutical Compositions

The PS for use in the methods of the invention can be formulated into an appropriate pharmaceutical composition for administering to subjects with DPN. Pharmaceutical compositions are typically formulated to provide a therapeutically effective amount of PS and may further comprise a pharmaceutically acceptable excipient.

Neuropathic pain associated with DPN can occur at various sites on the body. However, as outlined above, DPN tends to affect peripheral nerves in the upper and lower limbs, and thus the extremities, explaining the 'stocking and glove' distribution experienced by these patients. Therefore, a particularly useful pharmaceutical composition comprising PS is one which can be applied directly to peripheral locations experiencing neuropathic pain, for example the upper and lower limbs of the subject. In addition, the pharmaceutical composition comprising PS may be applied to those locations experiencing one or more sensory symptoms of DPN. Accordingly, the pharmaceutical composition comprising PS may be formulated for topical administration. In particular, the pharmaceutical composition comprising PS may be formulated for dermal administration, in particular to the skin of the upper and/or lower limbs of the subject.

In some embodiments, the pharmaceutical composition comprising PS may be formulated as a semi-solid or liquid. Therefore, the pharmaceutical composition comprising PS may be formulated as a cream, gel (e.g., a hydrogel), lotion, ointment, foam, and/or spray. These compositions differ in their relative concentrations of oils and water, which causes the compositions to have different densities. Altering the density of the formulation is a way in which exposure of the affected area to the pharmaceutical composition can be controlled. For example, a less dense formulation, which requires rubbing in until it has been absorbed, may result in a shorter exposure time. Alternatively, a more dense formulation, which is not readily absorbed, may allow prolonged exposure of the area to the pharmaceutical composition. The skilled person is aware of formulating topical pharmaceutical compositions so as to modify the relative exposure of the area to the active pharmaceutical ingredient.

In other embodiments, the pharmaceutical composition comprising PS may be formulated as a patch which can be applied to the skin. The patch may be manufactured in such a way as to ensure controlled release of PS to the affected area.

Formulations suitable for topical administration and appropriate pharmaceutically acceptable excipients are well-known in the art. Exemplary formulations for topical administration are provided in WO 2019/067919, which is hereby incorporated by reference in its entirety.

In some embodiments, the formulation of PS suitable for topical administration may comprise PS at a concentration of about 0.5% w/w to about 15% w/w of the pharmaceutical composition. Accordingly, the PS may be at a concentration of 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5% w/w of the pharmaceutical composition. As an illustrative example, when formulated as a topical cream, the PS may be at a concentration of less than or equal to 8% w/w of the pharmaceutical composition, for example about 5% w/w of the pharmaceutical composition, in particular about 3% w/w of the pharmaceutical composition. As a further illustrative example, when formulated as a gel, the PS may be at a concentration of less than or equal to 8% w/w of the pharmaceutical composition, for example less than or equal to 5% w/w of the pharmaceutical composition, in particular less than or equal to 3% w/w of the pharmaceutical composition, for example about 2% or about 1% w/w of the pharmaceutical composition. In particular formulations, for example when formulated as a hydrogel or an ointment, the PS may be at a concentration of 5% w/w of the pharmaceutical composition.

A single application to both hands (i.e., the gloves) may require less than about 5 ml of the pharmaceutical composition, for example about 3 ml of the pharmaceutical composition (i.e., about 1.5 ml of the pharmaceutical composition per hand). A single application to both feet (i.e., the stockings) may require less than about 6 ml of the pharmaceutical composition, for example about 4 ml of the pharmaceutical composition (i.e., about 2 ml of the pharmaceutical composition per foot).

The pharmaceutical composition comprising PS may alternatively be formulated for any other form of administration suitable for treating and/or preventing neuropathic pain associated with DPN. For example, the composition may be formulated for transdermal administration or injection, for example subcutaneous injection.

Dosing Regimens

The appropriate dosage regimen for PS for treating and/or preventing DPN will depend on such variables as the type and extent of progression of the pain (e.g., as determined by the "Pain Ladder" guideline from the World Health Organization), the severity of the pain (e.g., acute, subacute, or chronic), the age, weight, and general condition of the particular patient, formulation of the excipient, the route of administration, and the judgment of the attending clinician.

For topical administration, the PS can be administered to cover the one or more affected areas, for example the upper and lower limbs of the subject. In some embodiments, about 0.01 to about 5 g of the PS may be administered to the affected area. With respect to the size of the affected area, the PS may be administered at about 0.005-0.25 g/10 cm$^2$ of affected area. Therefore, the PS may be administered at about 0.005 g/10 cm$^2$, 0.01 g/10 cm$^2$, 0.05 g/10 cm$^2$, 0.1 g/10 cm$^2$, 0.15 g/10 cm$^2$, 0.2 g/10 cm$^2$ or 0.25 g/10 cm$^2$ of affected area.

The PS for use in topical administration in some instances may be applied and then removed from the affected area (e.g., by washing off) before reapplication. In some instances the PS is washed off after a certain period of time. Alternatively, as the analgesic effect may reduce over time and reapplication may be necessary, in some instances the PS is not washed off and instead PS is simply reapplied to the affected area after passing of the appropriate dosing period. For example, PS may be applied to the affected area and left on the affected area (before removal or reapplication) for between about 0.5 hours and about 5 hours. Accordingly, PS may be applied topically and left on the affected area (before removal or reapplication) for about 0.5 hours, for about 1 hour, for about 2 hours, for about 3 hours, for about 4 hours, or for about 5 hours.

As neuropathic pain associated with DPN is chronic, it is necessary to repeat topical administration of PS. Accordingly, the PS may be applied topically 1 to 4 times a day. Therefore, the PS may be applied once a day, twice a day, three times a day, or four times a day. With particular formulations of PS, for example a hydrogel or an ointment with a PS concentration of about 5% w/w of the pharmaceutical composition, the formulation may be applied topically three times a day. In more severe cases, a further application of PS may be applied about 0.5 hours after each application.

The PS may have a long-lasting analgesic effect and thus can be administered less frequently. For example, the PS can be administered topically less than once a day, for example once every other day. Indeed, for those patients experiencing long-term analgesia with a single administration, the PS may be administered topically less than once a week, for example once a fortnight.

For topical administration of some pharmaceutical compositions, it is useful to cover the affected area, for example with a dressing (e.g., a plastic wrap or film), after the pharmaceutical composition has been applied, for example to ensure appropriate amount of the composition can be applied for an appropriate time. Therefore, after topical application of the PS, the affected area may be dressed.

In some embodiments, the PS may be administered topically in the form of a patch, for example a medicated plaster. The use of a patch may allow the dosing interval and/or dosing frequency to be reduced, for example due to the patch ensuring controlled release of the PS. Accordingly, the patch may be applied to the affected area once a day, less than twice a day, less than three times a day, or less than four times a day.

The administration of the PS may continue as long as necessary. For example, the PS may be administered for more than 1, 2, 3, 4, 5, 6, 7, 14, 28, 56, or 84 days. As noted above, the PS can be administered chronically on an ongoing basis for the treatment of chronic effects, for example for at least 3 months. Accordingly, in some cases, continuous dosing is achieved and maintained as long as necessary. The PS may be administered intermittently according to the recurrence of the neuropathic pain and/or associated sensory symptoms.

The PS can be used for the treatment and/or prevention of DPN in mammals. For example the subject may be a human.

As noted above, PS can be formulated into an appropriate pharmaceutical composition for administering to subjects with DPN. Accordingly, the PS may be administered according to the dosing regimens above in an appropriate pharmaceutical composition.

A person having ordinary skill in the art understands that, in certain embodiments, dosages of such compounds may be adjusted depending upon the mammal to be treated. For example, the treatment of rats is described herein and such dosages may or may not be revised upon the administration of PS to a human. However, a person having ordinary skill in the art may, if necessary, convert the dosages provided herein as set forth in Guidance for Industry: Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005. A human equivalent dose (HED) may be determined from an animal dose, the animal dose may be multiplied by the following conversion factors, to provide units in mg/kg: mouse=0.08, hamster=0.13, rat=0.16, ferret=0.19, guinea pig=0.22, rabbit=0.32, dog=0.54, monkey=0.32, marmoset=0.16, squirrel monkey=0.19, baboon=0.54, micropig=0.73, and mini-pig=0.95.

Pharmaceutically Acceptable Forms of PS

The pharmaceutical composition comprising PS can contain a pharmaceutically acceptable form of PS. The pharmaceutically acceptable form may be a solvate, derivative, and/or prodrug.

Solvates

As used herein, the term "solvate" refers to a compound that further includes a stoichiometric or non-stoichiometric amount of solvent bound by non-covalent intermolecular forces. Where the solvent is water, the solvate is a hydrate. The pharmaceutically acceptable form of PS may include a solvate of PS, for example a solvate of PS-I and/or PS-II. In some embodiments, the solvate includes at least 1 molecule of solvent. In some embodiments, the solvate includes less than 1 molecule of solvent. In some embodiments, the solvate is a hydrate.

Isotopes

The pharmaceutically acceptable form of PS may include an isotopically labelled derivative of PS-I. The pharmaceutically acceptable form of PS may include an isotopically labelled derivative of PS-II. An isotopically labelled derivative is a compound that is identical to PS, except that one or more atoms are replaced by an atom having an atomic mass or mass number different from the atomic mass or mass number usually found in nature. In some embodiments, the isotopically labelled derivative of PS includes one or more isotopes of hydrogen, carbon, oxygen, phosphorus, and fluorine. In some embodiments, the isotopically labelled derivative of PS includes one or more isotopes of $^2H$, $^3H$, $^{13}C$, $^{14}C$, $^{18}O$, $^{17}O$, $^{31}P$, $^{32}P$, $^{35}S$, and $^{18}F$, respectively.

In some embodiments, the isotopically labelled derivative of PS includes one or more isotopes of $^2H$ (e.g., deuterium). In some embodiments, the isotopically labelled derivative of PS includes one or more isotopes of $^3H$ (e.g., tritium). In some embodiments, the isotopically labelled derivative of PS includes one or more isotopes of $^{14}C$.

Derivatives and Prodrugs

The pharmaceutically acceptable form of PS may include a derivative of PS-I. The pharmaceutically acceptable form of PS may include a derivative of PS-II. In some embodiments, the derivative of PS (e.g., PS-I or PS-II) is a metabolite. In other embodiments, the pharmaceutically acceptable form of PS is a prodrug of PS, for example a prodrug of PS-I or a prodrug of PS-II.

A sulfone group can be structurally expressed as: R—S(=O)$_2$—R'. In some embodiments, the derivative of PS is a sulfone form of PS.

PS contains an organophosphate functional group. An organophosphate functional group can be structurally expressed as O=P(OR)$_3$, O=P(OR)$_2$(OR'), or O=P(OR)(OR')(OR"). For example, O=P(OR)$_2$(OR') can represent PS if R=CH$_2$CH$_3$ and R=the remainder of the molecule is as per PS in formula I or II (e.g., PS-I, PS-II, or a derivative thereof).

In some embodiments, the derivative of PS is PS wherein one of the ethoxy (e.g. —OCH$_2$CH$_3$) groups is an OH group, or a pharmaceutically acceptable salt thereof. In some embodiments, the derivative of PS is PS wherein both ethoxy (e.g. —OCH$_2$CH$_3$) groups are OH groups, or a pharmaceutically acceptable salt thereof.

The activity of PS demonstrated herein would be shared by pharmaceutically acceptable forms thereof. Therefore, the present invention provides pharmaceutically acceptable forms of PS for use in the methods of the invention.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: The Effect of PS in a Rat Model of DPN

DPN was induced via chemically-induced increases in blood glucose in rats, using streptozotocin (STZ). This is a well-established model for DPN (see Morrow, Current Protocols in Neuroscience (2004); 29(1): 1-11), in which the STZ, an antibiotic extract from *Streptomyces acromogenes*, selectively damages the β cells of the pancreas. As demonstrated, PS is effective in the treatment of DPN in which treatment starts after the neuropathy is established.

Methods

Sprague-Dawley rats were fasted for 4-6 hours before being injected intraperitoneally with 45 mg/kg STZ. This was performed for all experimental groups, except the naïve group. In order to prevent hypoglycaemic death, rats received 10% sucrose water as the sole water source for the first 48 hours after injection. In order to ensure only those rats considered diabetic (i.e., having non-fasting plasma glucose levels of >250 mg/dL) were included in the study, blood glucose was measured at 72 hours after the STZ injection.

Figure 3:
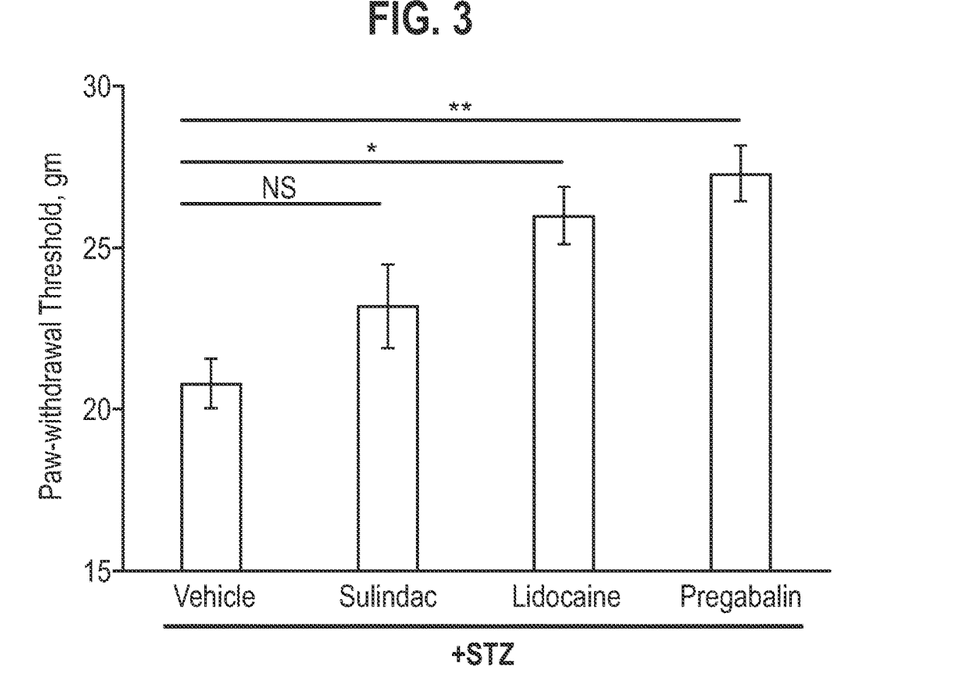
FIG. 3—effect of sulindac, lidocaine, and pregabalin on neuropathic pain associated with DPN.

Four weeks after STZ injection, the rats were randomised into treatment groups, as shown in FIG. 3. This delay between STZ injection and treatment allows the establishment of chronic pain (allodynia) associated with peripheral and central sensitisation. PS (as an 8% hydrogel) or vehicle control were administered topically to both hind paws of the rats 3 times a day for 3 weeks starting at week 4 after STZ injection. 0.7% sulindac hydrogel was applied 3 times a day for 1 week—this is the highest safe sulindac concentration for these animals. 5% lidocaine cream (a positive control) was applied only once to both hind paws of the rats 30 minutes before measurement of PWT. Finally, an additional positive control, pregabalin (at 10 mg/kg) or its vehicle were administered orally only once, one hour before measurement of PWT.

The rats were split into 8 study groups, with those in the experimental groups (1-4) having an average body weight of about 225 g, and those in the control groups (5-8) having an average body weight of about 335 g, as follows:

1. Group 1: naïve rats (n=5)
2. Group 2: STZ only (n=6)
3. Group 3: STZ plus vehicle (n=6)
4. Group 4: STZ plus PS (8% hydrogel) (n=7)
5. Group 5: STZ plus oral vehicle (n=8)
6. Group 6: STZ plus 0.7% sulindac hydrogel (n=7)
7. Group 7: STZ plus 5% lidocaine cream (n=8)
8. Group 8: STZ plus pregabalin (10 mg/kg) (n=7)

In order to determine the outcome of the treatment, mechanical allodynia was measured using the well-established method of von Frey filaments. In particular, a simplified up-down method for estimating paw withdrawal threshold (PWT) using von Frey filaments was used (as described in Bonin et al., Molecular Pain (2014); 10(26):1-10). The results of the PWT test are expressed as force applied (gm). The PWT test was performed at weeks 4, 5, and 7, depending on the administration protocol, with the first measurement being the baseline (i.e., demonstrating the efficacy of STZ in establishing DPN). The measurements on weeks 5 and 7 were performed 30 minutes after the last treatment with sulindac or PS, respectively. For completeness, the difference in average body weights of the rats in the experimental and control groups does not impact the ability to compare the results from these groups (i.e., the rats were simply obtained from different batches and respond in the same way to the experimental procedure).

Figure 1:
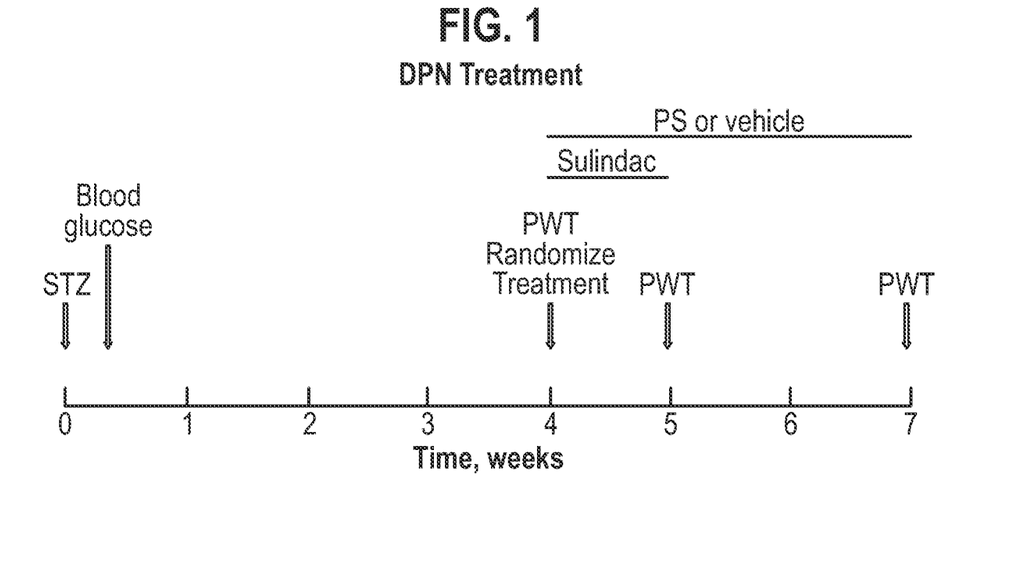
FIG. 1— schematic outline of the neuropathic pain associated with DPN treatment study. STZ is streptozotocin. PWT is paw withdrawal threshold test.

FIG. 1 provides an outline of the study.

Results

Figure 2:
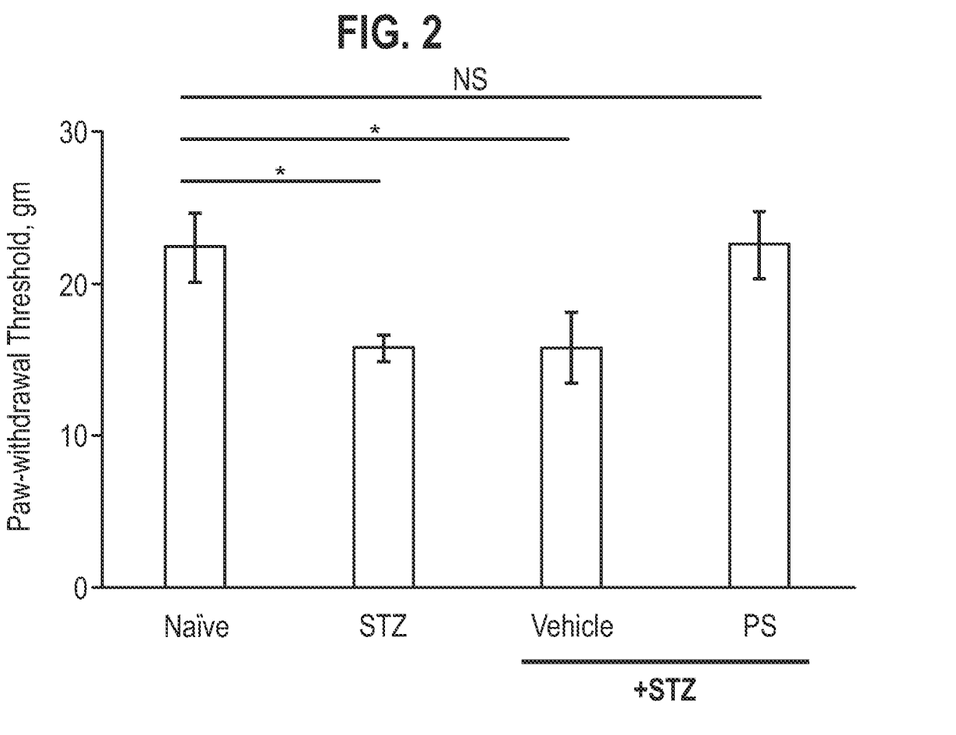
FIG. 2—effect of PS on neuropathic pain associated with STZ-induced DPN, compared to vehicle.

As displayed in FIG. 2, the administration of STZ resulted in a significant decrease in PWT ($p<0.02$ vs naïve rats) 4 weeks after administration. Therefore, the model established pain associated with DPN, as expected. The additional administration of vehicle had no significant effect on the PWT compared to STZ only, with the reduction in PWT relative to naïve rats similar to STZ alone. However, administration of PS achieved a significant increase in PWT compared to vehicle and STZ ($p<0.04$ and $p<0.01$, respectively), bringing the PWT back up to the threshold observed in naïve rats ($p<0.01$). The values, corresponding to FIG. 2, are provided in Table 1.

TABLE 1

PWT in the first 4 study groups

| Groups | PWT, gm Mean ± SEM | P values |
|---|---|---|
| Naïve | 22.4 ± 2.24 | |
| STZ only | 15.7 ± 0.84 | *$p < 0.02$ vs naive |
| STZ + vehicle | 15.8 ± 2.33 | NS vs STZ only |
| | | *$p < 0.01$ vs naive |
| STZ + PS | 22.5 ± 2.20 | NS vs naive |
| | | *$p < 0.04$ vs vehicle |
| | | *$p < 0.01$ vs STZ only |

Furthermore, as displayed in FIG. 3, administration of either vehicle or sulindac failed to suppress the reduced PWT caused by STZ (sulindac was not significantly different to vehicle). However, both lidocaine and pregabalin achieved significant increases in PWT compared to vehicle ($p<0.03$ and $p<0.009$ respectively). The values, corresponding to FIG. 3, are provided in Table 2.

TABLE 2

PWT in the second 4 study groups

| Groups | PWT, gm Mean ± SEM | P values |
|---|---|---|
| STZ + oral vehicle | 20.8 ± 1.5 | |
| STZ + sulindac | 23.2 ± 2.6 | NS vs vehicle |
| STZ + lidocaine | 26.0 ± 1.8 | *$p < 0.03$ vs vehicle |
| STZ + pregabalin | 27.3 ± 1.7 | ** $p < 0.009$ vs vehicle |

Conclusions

The topical administration of PS is efficacious in normalizing the neuropathic pain induced by diabetes in one of the most reliable animal models of the disease. Indeed, PS significantly increased the PWT in rats displaying neuropathic pain caused by STZ. Therefore, PS treats the neuropathic pain associated with DPN.

Whereas PS was effective, strikingly its non-phosphorylated 'parent' sulindac (a typical NSAID) failed to achieve a rescue in the PWT in the rat model and so failed to treat pain associated with DPN. This was the case even though the sulindac was administered at a maximum non-toxic dose and in the same manner and formulation as PS. The positive controls, lidocaine and pregabalin, known to have central sites of action in analgesia, demonstrated a significant reduction in pain associated with DPN, as expected. Therefore, the efficacy observed for locally administered PS is more similar to the centrally acting positive controls than to its closely related parent compound.

Accordingly, PS is mechanistically distinct from its parent NSAID and may be acting in a manner more similar to the centrally acting agents. These observations serve to demonstrate the potential of PS in established neuropathic pain associated with DPN.

Example 2: The Effect of PS in Preventing Neuropathic Pain in a Rat Model of DPN DPN was induced via chemically-induced increases in blood glucose in rats, using streptozotocin (STZ). In order to establish a prevention model, the STZ was administered (on day 0) after initiation of treatment with PS (sulindac or vehicle) at day −2. As demonstrated, unlike sulindac, PS is effective in the prevention of neuropathic pain associated with DPN.

Methods

The animal model corresponds to that used for Example 1, but using a prevention protocol. As in Example 1, the outcome measure, determining the effect of the treatment on the prevention of mechanical allodynia, was the PWT test, using von Frey filaments. The measurements were taken at day −3, before treatment or induction of neuropathic pain associated with DPN, and again at the end of the study period (day 28).

The rats were randomised into treatment groups as follows, all having an average body weight of about 225 g.
1. Group 1: naïve rats (n=6)
2. Group 2: STZ only (n=8)
3. Group 3: STZ plus vehicle (n=8)
4. Group 4: STZ plus PS 8% (n=8)
5. Group 5: STZ plus sulindac 0.7% (n=8)
6. Group 6: STZ plus lidocaine cream 5% (n=8)

Each treatment group was subjected to a PWT assessment at day −3 in order to determine the baseline of mechanical allodynia. Subsequently, depending on the treatment group, rats were started on a treatment regimen of PS (8% hydrogel), sulindac (0.7% hydrogel) or vehicle, applied topically to both hind paws of the rats three times a day from day −2 and continued until day 28. For those rats in the lidocaine treatment group, lidocaine cream was applied only once to both hind paws of the rats 30 min before the final PWT measurement on day 28. On day 0, neuropathic pain associated with DPN was induced with the administration of STZ, and the blood glucose was checked on day 3. Four weeks after the administration of STZ, to provide sufficient time to allow the neuropathic pain associated with DPN (manifested as mechanical allodynia) to develop (see the STZ only group in FIG. 5), the rats were subjected to the paw withdrawal threshold test.

Figure 4:
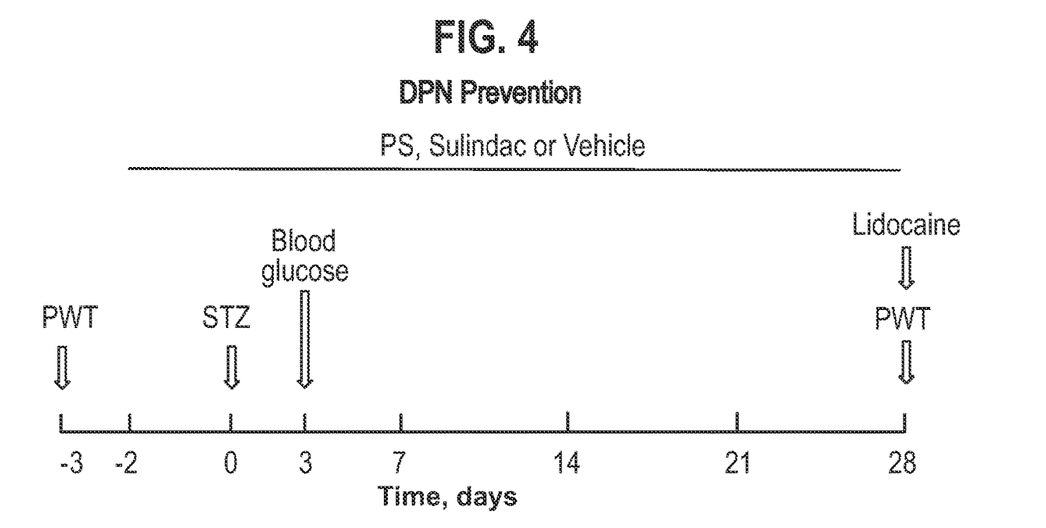
FIG. 4—schematic outline of the neuropathic pain associated with DPN prevention study. STZ is streptozotocin. PWT is paw withdrawal threshold test.

FIG. 4 provides an outline of the study.

Results

Figure 5:
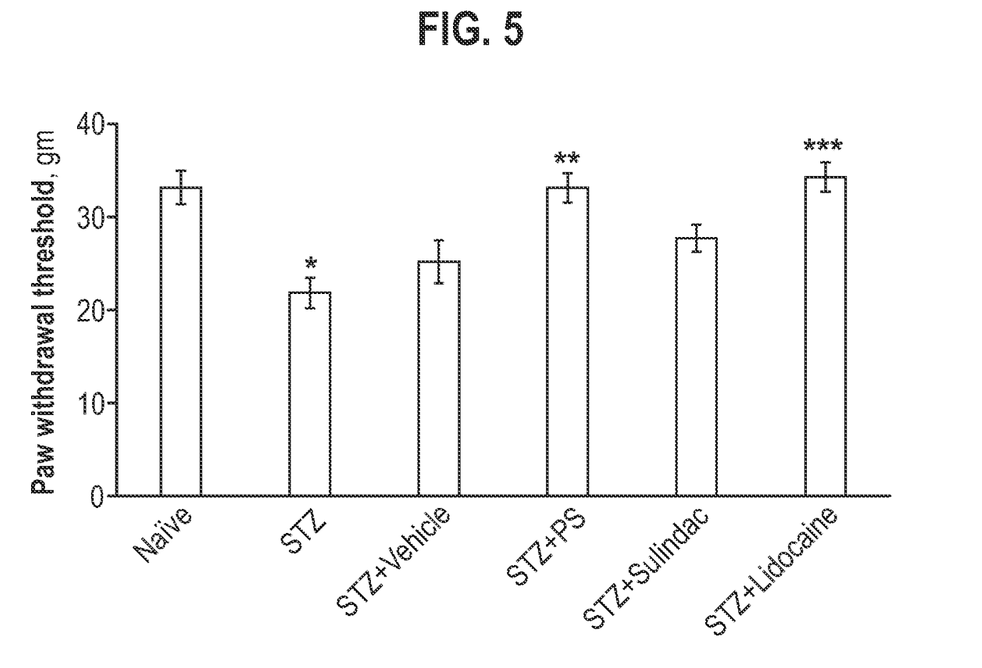
FIG. 5—effect of PS on prevention of neuropathic pain associated with DPN. *, $p<0.0001$ (STZ vs naïve); , $p<0.004$ (PS vs vehicle); *, $p<0.001$ (lidocaine vs vehicle).

As displayed in FIG. 5, the administration of STZ resulted in a significant decrease in PWT (p<0.0001 vs naïve rats) 4 weeks after administration. Therefore, the model established neuropathic pain associated with DPN, as also achieved in Example 1. The additional administration of vehicle had no significant effect on the PWT compared to STZ only. However, administration of PS achieved a significant increase in PWT compared to vehicle (p<0.004), bringing the PWT back up to the threshold observed in naïve rats. The effect of PS on PWT corresponded to that achieved using lidocaine, which significantly increased the PWT compared to vehicle (p<0.001). However, the administration of sulindac showed no significant effect on PWT compared to the vehicle. Indeed, PS showed a significant effect on PWT compared to the effect achieved with sulindac.

The values, corresponding to FIG. 5, are provided in Table 3.

TABLE 3

PWT in the prevention of neuropathic pain experiment

| Groups | von Frey, gm mean ± SEM | p values |
|---|---|---|
| Naïve | 33.2 ± 1.8 | |
| STZ | 21.8 ± 1.6 | p < 0.0001 vs Naïve |
| STZ + vehicle | 25.2 ± 2.3 | NS vs STZ |
| STZ + PS | 33.1 ± 1.6 | p < 0.004 vs vehicle: p < 0.02 vs sulindac |
| STZ + sulindac | 27.7 ± 1.4 | NS vs vehicle |
| STZ + lidocaine | 34.3 ± 1.6 | p < 0.001 vs vehicle p < 0.005 vs sulindac |

Conclusions

Similar to the observations with respect to the treatment experiment in Example 1, the topical administration of PS is efficacious in preventing neuropathic pain associated with DPN, as shown by the significant increase in PWT in those rats prophylactically administered PS.

In contrast to PS, sulindac (again dosed at its maximum non-toxic dose and in a regimen and frequency corresponding to that used for PS) failed to prevent neuropathic pain associated with DPN. The positive control, lidocaine, known to have a central site of action in analgesia, effectively prevented neuropathic pain associated with DPN, achieving a similar normalisation of the PWT as achieved by PS. Therefore, the prophylactic efficacy observed for locally administered PS is more similar to the centrally acting positive control than to its closely related parent compound, sulindac.

Accordingly, supporting the observations in Example 1, this experiment confirms that PS is mechanistically distinct from its parent NSAID even in the prophylactic setting, demonstrating therapeutic efficacy similar to the centrally acting lidocaine. These observations serve to confirm the potential of PS in prevention of neuropathic pain associated with DPN.

Example 3: Pharmacokinetics and Biodistribution of PS

Given the ability of PS to treat and prevent neuropathic pain associated with DPN, in particular with efficacy corresponding to that of centrally acting agents (e.g., pregabalin and lidocaine), the site of action of PS was investigated. Despite being topically administered, PS was found to traverse within nerves from the periphery towards the spinal cord.

Methods

PS 8% ointment was applied topically to each hind paw (50 μl per paw) with gentle rubbing. At 0.5, 1, 3, 5, 12, 18, and 24 h, mice (n=4-5 mice/time point) were euthanized with $CO_2$ inhalation. Blood was drawn immediately after death. Tissues, including paw skin, paw muscle, leg muscle, the sciatic nerve and lumbar DRG bilaterally were dissected quickly, immediately frozen in liquid nitrogen and stored at −80° C. until analyzed.

As previously described (Wen et al., Int J Pharm (2019); 557:273-279), each plasma sample was mixed with double volume of acetonitrile and centrifuged at 13,200 rpm for 15 min Tissue samples were weighed, ddH$_2$O (100-300 μL, depending on tissue weight) was added and they were homogenized. Following addition of acetonitrile (twice the volume of the homogenate), the mixture was sonicated for 10 min, centrifuged at 13,200 rpm for 15 min, and analyzed by HPLC, as reported (Wen et al., 2019). The limit of quantitation is 0.1 μM for PS and 0.05 μM for sulindac, sulindac sulfone, sulindac sulfide and their glucuronidated derivatives.

Results

Figure 6:
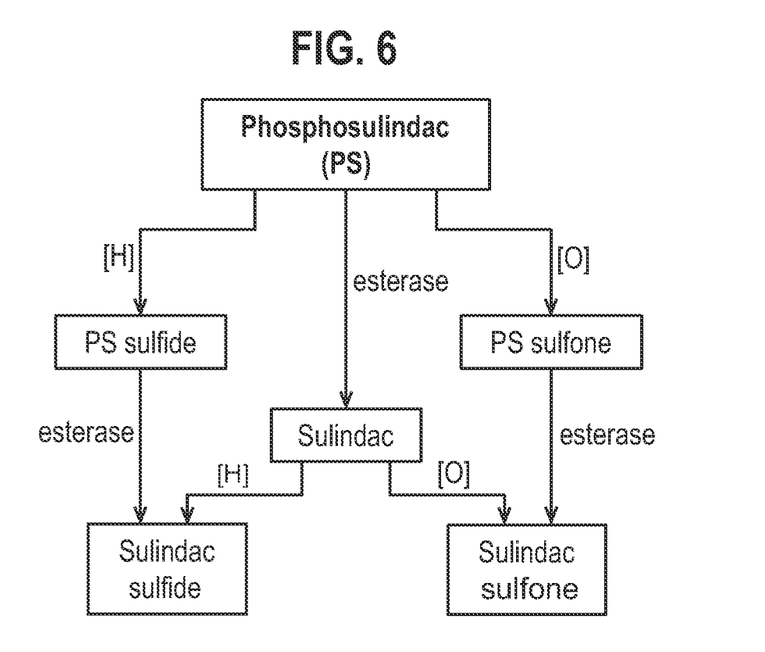
FIG. 6—schematic outline of the metabolism of PS.

PS can be rapidly metabolized into several metabolites both in vitro and in vivo that include PS sulfide, PS sulfone, sulindac, sulindac sulfide and sulindac sulfone (FIG. 6). Glucuronides of sulindac and its metabolites, mainly forming in the liver, have also been identified. Since the metabolism and PK/biodistribution of PS vary depending on its route of administration, we studied both in normal mice in which PS was administered topically to their hind paws, with particular attention to the sciatic nerve and the dorsal root ganglia (DRG) that are affected in DPN.

Figure 7:
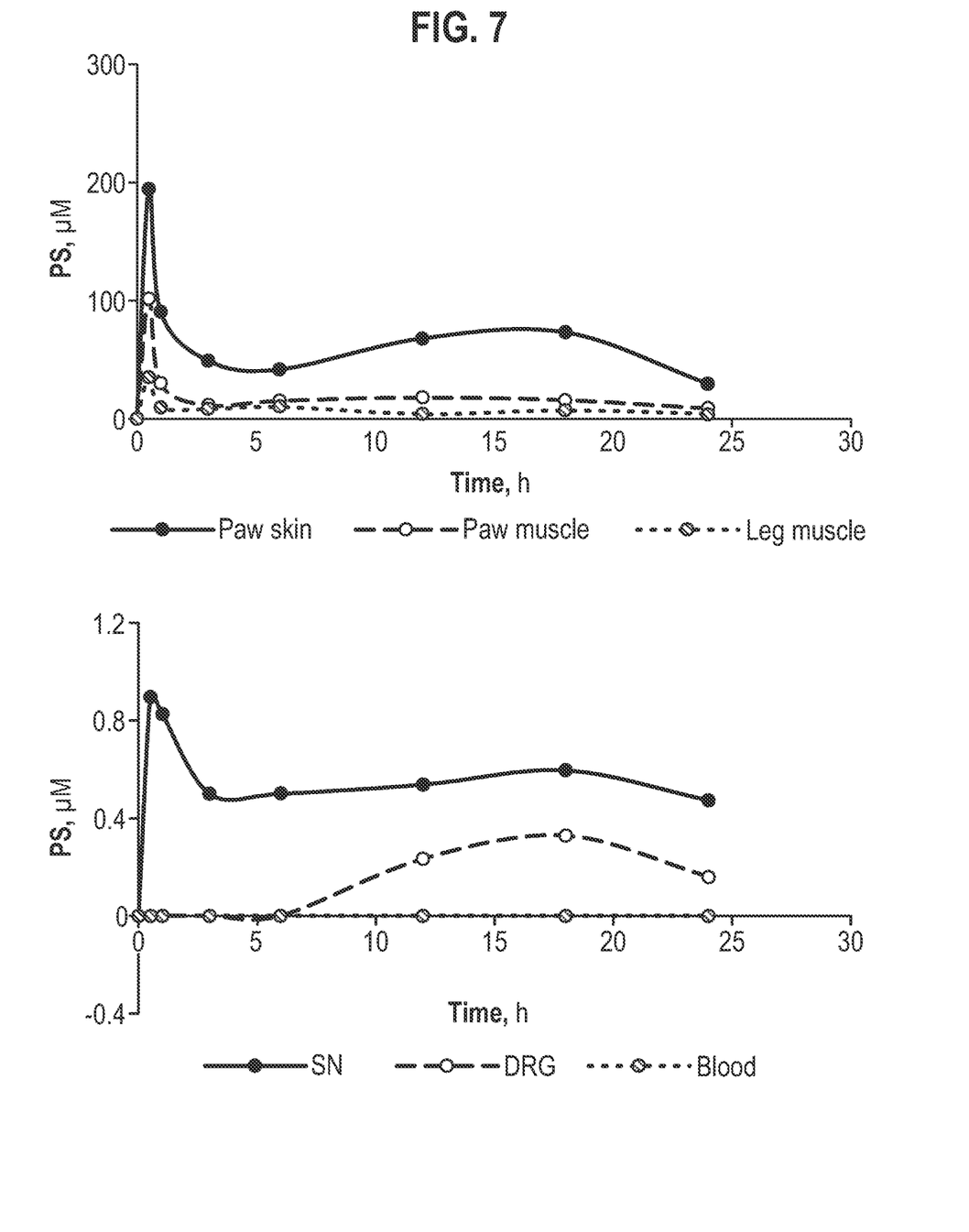
FIG. 7—biodistribution of PS in different tissues upon topical administration. SN=sciatic nerve. DRG=dorsal root ganglia.

As shown in FIG. 7 and Table 4, PS was detected in paw skin, the site of its application, the muscles underneath the skin, leg muscles, the sciatic nerve, and DRG. As expected (Xie et al., Br J Pharmacol (2012a); 165:2152-2166), no PS was detected in the systemic circulation.

The concentration of PS progressively decreased from the skin to its most distant DRG, evidenced by the respective values of both $C_{max}$ (from 194.7±5.3 μM to 0.3±0.1 μM) and $AUC_{0-24h}$ (from 1,609.8 μM·h to 4.5 μM·h). The $T_{max}$ of PS was the same in all tissues (0.5 h) with the exception of DRG that showed a prolonged $T_{max}$ (18 h), reflecting perhaps the manner in which PS reaches it, as discussed below. Another interesting feature is the difference in $t_{1/2}$ of the skin and the muscles, which is within a relatively narrow range (11.4-20.6 h), in contrast to the much-prolonged value of 57.4 h in the sciatic nerve and the likely even more prolonged value in DRG, which could not be determined with reasonable accuracy.

These differences indicate differential metabolic capacity regarding PS between the nerve and skin and muscles.

TABLE 4

PK parameters of PS in mouse tissue and peripheral blood of normal mice

| Tissue | $C_{max}$, μM mean ± SEM | $T_{max}$, h | $T_{1/2}$, h | $AUC_{0-24h}$, μM·h |
|---|---|---|---|---|
| Paw skin | 194.7 ± 5.3 | 0.5 | 16.1 | 1,609.8 |
| Paw muscle | 101.7 ± 4.6 | 0.5 | 11.4 | 411.2 |
| Leg muscle | 35.0 ± 3.6 | 0.5 | 20.6 | 171.6 |
| SN | 0.9 ± 0.1 | 0.5 | 57.4 | 12.0 |
| DRG | 0.3 ± 0.1 | 18 | * | 4.5 |
| Blood | ** | ** | ** | ** |

*, cannot be determined.
**, cannot be calculated because intact PS was undetectable.
N = 4-5 mice/time point.

Figure 8:
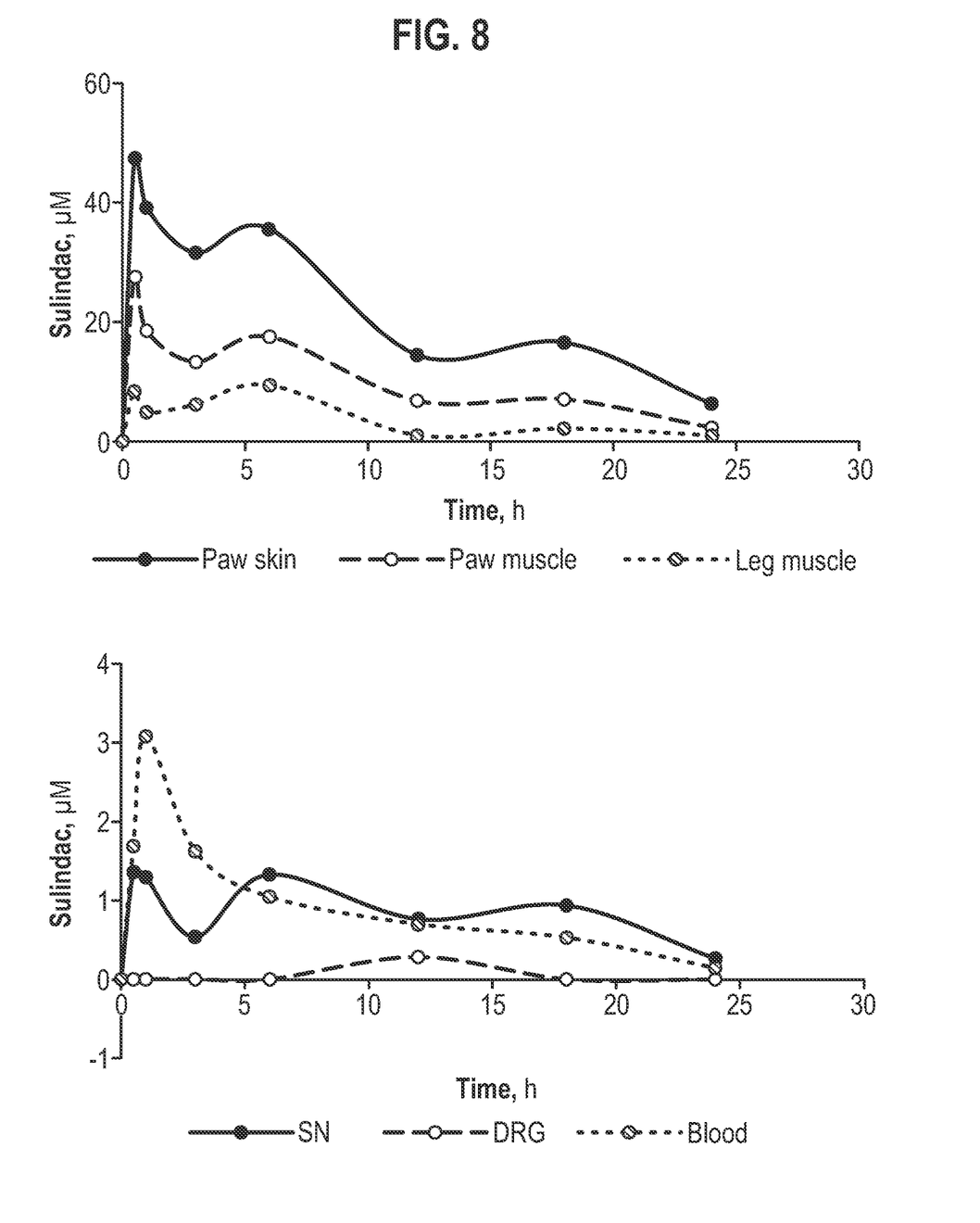
FIG. 8—biodistribution of the metabolites of PS in different tissues upon topical administration of PS. SN=sciatic nerve. DRG=dorsal root ganglia.

Only three metabolites of PS were detected: sulindac, sulindac sulfone, and sulindac sulfide, (FIG. 8 and Table 5). No glucuronidated products were detected. Sulindac was the quantitatively dominant metabolite, with sulindac sulfide and sulindac sulfone levels being <20% of those of sulindac. Sulindac levels were around 25% of those of PS in all tissues except the sciatic nerve (higher) and DRG (equal).

TABLE 5

PK parameters of sulindac in mouse tissue and peripheral blood of normal mice

| Tissue | $C_{max}$, μM mean ± SEM | $T_{max}$, h | $T_{1/2}$, h | $AUC_{0-24h}$, μM·h |
|---|---|---|---|---|
| Paw skin | 47.4 ± 3.8 | 0.5 | 47.4 | 516.6 |
| Paw muscle | 27.5 ± 3.3 | 0.5 | 7.9 | 238.6 |
| Leg muscle | 8.4 ± 2.1 | 0.5 | 8.2 | 71.8 |
| SN | 1.4 ± 0.3 | 0.5 | 12.3 | 22.3 |
| DRG | 0.3 ± 0.1 | 12 | * | 1.6 |
| Blood | 3.1 ± 0.5 | 1 | 6.2 | 21.2 |

*, cannot be determined.
N = 4-5 mice/time point.

The presence of PS even in small amounts in the sciatic nerve ($C_{max}$=0.9±0.1 μM; $AUC_{0-24h}$=12.0 μM·h) and DRG ($C_{max}$=0.3±0.1 μM; $AUC_{0-24h}$=4.5 μM·h) is of particular interest, since both are targets of neuropathic pain associated with DPN. The absence of PS in the circulation, the very high $T_{max}$ of DRG compared to all others, and the lower levels of PS in DRG compared to the sciatic nerve suggest that PS reached the DRG by traversing from the skin through the sciatic nerve.

Conclusions

These experiments demonstrate that topically administered PS can reach key sites of action known to be involved in the generation of neuropathic pain associated with DPN (i.e., the sciatic nerve and dorsal root ganglion). Furthermore, in light of its rapid metabolism in the bloodstream, the results demonstrate that PS reaches these site of action by traversing along peripheral neurons (e.g., the sciatic nerve) towards the central nervous system, being found in meaningful concentrations in the DRG. Therefore, without wishing to be bound by theory, these observations confirm that PS performs its analgesic activity directly on neurons and likely within central sites of action, similar to the activity of centrally acting analgesics such as lidocaine and pregabalin. This site of action reflects the equivalent efficacy of PS and pregabalin and lidocaine in the treatment and prevention of neuropathic pain associated with DPN observed above.

Example 4: Summary of Observations

The observations herein demonstrate an unprecedented analgesic activity of PS in preventing and treating neuropathic pain associated with DPN using a well-established animal model. Accordingly, the experiments above demonstrate that PS is able to reduce neuropathic pain signalling caused by DPN. Upon topical administration, PS is shown to follow an ascending trajectory along peripheral neurons (e.g., the sciatic nerve) towards the spinal cord and can achieve a significant analgesic effect on neuropathic pain associated with DPN. The topical route provides low systemic clearance, reduced drug interactions, increased patient tolerability, and facile combination with oral medications.

These observations demonstrate a previously unrecognised activity and therapeutic utility of PS, a compound which falls within the broader class of NSAIDs but does not share all of the properties of this family of compounds. In fact, in contrast to the observations for the NSAID, sulindac, the data herein demonstrate that the activity of PS is more similar to analgesic agents which target neuronal activity directly, and with potential to act at both peripheral and central sites. Indeed, the results above confirm that PS can reduce pain from allodynia which is known to include pain generated via peripheral and central sensitisation. The model was established for four weeks prior to treatment randomisation thus clearly establishing central sensitisation demonstrated by the allodynia. Therefore, without wishing to be bound by theory, PS is having a direct effect on neuronal pain signalling, similar to the mechanism of action of established anaesthetics. In fact, the results show the ability of PS to reduce pain signalling from peripheral and central sensitisation, implicating both peripheral and central sites of action for the analgesic activity of this compound. Of course, this activity is distinct from the established role of PS, and typical NSAIDs, as anti-inflammatory agents.

Earlier observations regarding the activity of PS are limited to its anti-inflammatory activity. For example, WO 2019/067919 suggests a role for PS in the treatment of DED, using an acute DED model, in which concanavalin A (ConA) is administered to rabbit lacrimal glands concurrently with PS. In this context, the anti-inflammatory activity of PS results in a limited inflammatory response to ConA, thus preventing the establishment of DED. These observations confirm the anti-inflammatory activity of PS and suggest its utility in preventing establishment and maintenance of inflammatory components of DED. The observations in this acute DED model fail to provide any evidence of the ability of PS to act directly on nerves to reduce nerve signalling caused by neuropathic pain. Any reduction in pain in this acute DED model can be assumed only to be a consequence of PS inhibiting the inflammatory response (i.e., the pathology responsible for triggering activation of the pain sensors). In fact, the results of the DED model suggest that PS improves corneal sensitivity, implicating an increase in nociception, the opposite effect to that desired for an analgesic. Of course, irrespective of any suggestion towards analgesic activity of PS, such activity observed in an acute DED model provides no indication of a corresponding activity in neuropathic pain, and certainly not in neuropathic pain associated with DPN.

The experiments herein were performed in a specific animal model for neuropathic pain associated with DPN. As outlined above, the use of appropriate animal models is critical for demonstrating the potential efficacy of a compound in a particular type of neuropathic pain. Efficacy of a drug against pain arising from peripheral neuropathies cannot be extrapolated from its efficacy against other forms of pain, or even other forms of neuropathic pain. Indeed, specific forms of neuropathic pain differ in their pathogenesis and thus require therapeutic agents with different activities for their treatment and/or prevention. Therapies need to be designed according to the specific pathophysiology of the neuropathic pain and tested in an appropriate model. For example, DPN causes extensive nerve damage by metabolic abnormalities of diabetes including microvessel ischemia, increased activity in the polyol pathway of glucose metabolism, activation of protein kinase C, lack of insulin-mediated neurotrophic effects and altered fatty acid pathways, while other neuropathies may occur as a result of demyelination or impairment of calcium metabolism, for example due to administration of toxic chemotherapeutic agents. Therefore, the effects on both large and small fibres differs between DPN and other forms of neuropathy on the basis of their specific pathophysiology. The only reliable determination of efficacy of a compound in treating the neuropathic pain caused by such pathophysiology is to test the compound in an appropriate neuropathic pain model of DPN, as shown above. Without these observations, any indication of pain relieving activity of PS in the context of neuropathic pain associated with DPN is lacking.

The observations herein demonstrate that PS has therapeutic utility beyond that suggested for typical NSAIDs. Indeed, Moore et al. (Cochrane Database of Systematic Reviews (2015); 10: 1-25), outlined that NSAIDs have no therapeutic efficacy in peripheral neuropathic pain. The distinct activity of PS compared to typical NSAIDs is confirmed by the comparison with its parent compound, sulindac, in the experiments above. Sulindac failed to reduce established allodynia (i.e., caused by sensitisation of peripheral and central neurons), indicating that, unlike PS, sulindac does not provide a direct analgesic effect on damaged neurons in neuropathic pain caused by DPN. The reason for the absence of any response to sulindac in this model is likely that the pain is caused by neuropathic nerve damage once the pain of allodynia is established, rather than by inflammation (i.e., any anti-inflammatory activity of sulindac is not sufficient to prevent neuropathic pain). Accordingly, the analgesic activity of PS is unique and not shared by closely related NSAIDs. Based on the observations herein for sulindac, any alleged analgesic activity of NSAIDs observed in the prior art is a reflection of their anti-inflammatory activity (i.e., stopping the initial triggers causing the pain) rather than an actual analgesic activity directed towards nerve signalling (i.e., that would result in a reduction in pain caused by nerve damage and sensitisation). Indeed, if typical NSAIDs, for example sulindac, were capable of acting directly on neurons with analgesic activity, then sulindac would have been expected to reduce the allodynia observed in the model above.

Therefore, the present inventor has demonstrated a new surprising activity for PS in the treatment and/or prevention of neuropathic pain associated with DPN. As outlined above, this activity goes beyond the anti-inflammatory activity previously observed for PS and related NSAIDs. In fact, unlike typical NSAIDs, the observations herein demonstrate that PS has a direct activity on peripheral and central nerves, similar to the site and mechanism of action of established analgesics, such as lidocaine and pregabalin. Furthermore, the ease by which PS can be administered, for example topically, and its limited adverse effects (Mackenzie et al. (2010) *Gastroenterology* 139(4): 1320-32) render it an improved therapy for neuropathic pain associated with DPN compared even to these centrally acting analgesics.

It will be understood that the inventor's work has been described above by way of example only and modifications may be made while remaining within the scope and spirit of the invention.

The invention claimed is:

1. A method of treating and/or preventing neuropathic pain associated with diabetic peripheral neuropathy (DPN) comprising administering a therapeutically effective amount of phosphosulindac (PS) to a subject in need thereof such that neuropathic pain associated with DPN is treated and/or prevented.

2. The method of claim 1, wherein treating the neuropathic pain comprises reducing or eliminating the neuropathic pain, or reducing or eliminating one or more of the sensory symptoms associated with DPN.

3. The method of claim 1, wherein preventing the neuropathic pain comprises decreasing the incidence of the neuropathic pain, or decreasing the incidence of one or more of the sensory symptoms associated with DPN.

4. The method of claim 2, wherein the one or more sensory symptoms is selected from paresthesia, burning sensations, and shooting sensations.

5. The method of claim 4, wherein the paresthesia includes one or more of numbness, tingling, pricking, or formication.

6. The method of claim 1, wherein PS reduces, eliminates, or decreases the incidence of the neuronal signalling involved in the sensation of pain, or the incidence of pain generated via peripheral sensitisation, or the incidence of pain generated via central sensitisation, or the incidence of pain signalling occurring centrally, or the incidence of pain signalling occurring in the sciatic nerve, or the incidence of pain signalling occurring in the dorsal root ganglion.

7. The method of claim 1, wherein the neuropathic pain is allodynia.

8. The method of claim 7, wherein the allodynia is mechanical allodynia and/or thermal allodynia.

9. The method of claim 1, wherein the neuropathic pain is hyperalgesia.

10. The method of claim 1, wherein the subject is human.

11. The method of claim 1, wherein PS has the formula I (PS-I):

(I)

12. The method of claim 1, wherein PS has the formula II (PS-II):

(II)

13. The method of claim 1, wherein the therapeutically effective amount of PS is administered as a pharmaceutical composition comprising PS and a pharmaceutically acceptable excipient.

14. The method of claim 13, wherein the pharmaceutical composition comprising PS is formulated for topical administration.

15. The method of claim 14, wherein the pharmaceutical composition comprising PS is formulated as a semi-solid.

16. The method of claim 14, wherein the pharmaceutical composition comprising PS is formulated as a liquid.

17. The method of claim 14, wherein the pharmaceutical composition comprising PS is a cream, a gel, a hydrogel, a lotion, an ointment, or a spray.

18. The method of claim 14, wherein the pharmaceutical composition comprising PS is formulated as a patch.

19. The method of claim 13, wherein the pharmaceutical composition comprises PS at a concentration of about 0.5% to about 15% w/w of the pharmaceutical composition.

20. The method of claim 13, wherein the pharmaceutical composition comprises PS at a concentration chosen from about 15%, about 14.5%, about 14%, about 13.5%, about 13%, about 12.5%, about 12%, about 11.5%, about 11%, about 10.5%, about 10%, about 9.5%, about 9%, about 8.5%, about 8%, about 7.5%, about 7%, about 6.5%, about 6%, about 5.5%, about 5%, about 4.5%, about 4%, about 3.5%, about 3%, about 2.5%, about 2%, about 1.5%, about 1%, and about 0.5% w/w of the pharmaceutical composition.

21. The method of claim 13, wherein the pharmaceutical composition comprises PS at a concentration of less than or equal to 8% w/w of the pharmaceutical composition.

22. The method of claim 13, wherein the pharmaceutical composition comprises PS at a concentration of less than or about equal to 3% w/w of the pharmaceutical composition.

23. The method of claim 13, wherein the PS is administered at about 0.005 g/10 cm$^2$ to about 0.25 g/10 cm$^2$ of affected area.

24. The method of claim 13, wherein the PS is administered in an amount chosen from about 0.005 g/10 cm$^2$ of affected area, at about 0.01 g/10 cm$^2$ of affected area, at about 0.05 g/10 cm$^2$ of affected area, at about 0.1 g/10 cm$^2$ of affected area, at about 0.15 g/10 cm$^2$ of affected area, at about 0.2 g/10 cm$^2$ of affected area, and at about 0.25 g/10 cm$^2$ of affected area.

25. The method of claim 13, wherein the PS is applied to an affected area and left on the affected area for between about 1 hour and about 5 hours.

26. The method of claim 13, wherein the PS is applied to an affected area and left on the affected area for a time period chosen from about 0.5 hours, about 1 hour, about 2 hours, about 3 hours, about 4 hours, and about 5 hours.

27. The method of claim 25, wherein the PS is further removed from the affected area after being left on the affected area for between about 1 hour and about 5 hours.

28. The method of claim 25, wherein a second or further application of PS is applied to the affected area.

29. The method of claim 13, wherein the PS is applied once a day, twice a day, three times a day, or four times a day.

* * * * *